United States Patent
Marambaud

(10) Patent No.: US 12,239,636 B2
(45) Date of Patent: Mar. 4, 2025

(54) COMBINED SIROLIMUS AND NINTEDANIB THERAPY FOR VASCULAR LESIONS AND HEREDITARY HEMORRHAGIC TELANGIECTASIA

(71) Applicant: THE FEINSTEIN INSTITUTES FOR MEDICAL RESEARCH, Manhasset, NY (US)

(72) Inventor: Philippe Marambaud, Astoria, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 915 days.

(21) Appl. No.: 17/274,725

(22) PCT Filed: Sep. 24, 2019

(86) PCT No.: PCT/US2019/052551
§ 371 (c)(1),
(2) Date: Mar. 9, 2021

(87) PCT Pub. No.: WO2020/068719
PCT Pub. Date: Apr. 2, 2020

(65) Prior Publication Data
US 2021/0346355 A1 Nov. 11, 2021

Related U.S. Application Data

(60) Provisional application No. 62/736,564, filed on Sep. 26, 2018.

(51) Int. Cl.
| | | |
|---|---|---|
| A61K 31/436 | (2006.01) |
| A61K 31/496 | (2006.01) |
| A61P 7/04 | (2006.01) |
| A61P 7/06 | (2006.01) |

(52) U.S. Cl.
CPC .......... *A61K 31/436* (2013.01); *A61K 31/496* (2013.01); *A61P 7/04* (2018.01); *A61P 7/06* (2018.01)

(58) Field of Classification Search
CPC ....... A61K 31/436; A61K 31/496; A61P 7/04; A61P 7/06
See application file for complete search history.

(56) References Cited

FOREIGN PATENT DOCUMENTS

WO 2017004266 A1 1/2017

OTHER PUBLICATIONS

Birgegard Ther Clin Risk Manag 2008, 4 (2), 527-539.*
Skaro et al. Ann. Intern. Med. 2006, 144, 226-227.*
Hilberg et al. Cancer Res 2008, 68 (12), 4774-4782.*
International Search Report and Written Opinion dated Dec. 20, 2019 from PCT International Appln. No. PCT/US2019/052551.
Ruiz et al., "Tacrolimus Rescues the Signaling and Gene Expression Signature of Endothelial ALK1 Loss-of-Function and Improves HHT Vascular Pathology," Human Molecular Genetics, Sep. 14, 2017, vol. 26, No. 24, pp. 4786-4798.
Ardelean et al., "Anti-Angiogenic Therapeutic Strategies in Hereditary Hemorrhagic Telangiectasia," Frontiers in Genetics, vol. 6, Article 35, Feb. 2015, pp. 1-7.
Mumal, "Nintedanib Reduces Fibrosis and Blood Vessel Remodeling in Mice With Systemic Sclerosis, Study Shows," Scleroderma News, published on Oct. 19, 2017, retrieved from the internet on Nov. 15, 2019 at https://sclerodermanews.com/2017/10/19/mouse-study-shows-that-ofev-alleviates-manifestations-of-system-sclerosis/, 10 pages.
Ruiz et al., "Sirolimus Plus Nintedanib Treats Vascular Pathology in HHT Mouse Models," bioRxiv, Aug. 18, 2019, pp. 1-47.
MacKenzie Crist et al., "Examining the bleeding incidences associated with targeted therapies used in metastatic renal cell carcinoma," Critical Reviews in Oncology/Hematology, vol. 120, pp. 151-162, 2017, XP085299899, DOI: 10.1016/j.critrevonc.2017.10.014.
Andrea Mancuso et al., "Sorafenib efficacy for treatment of HCC recurrence after liver transplantation is an open Issue," Journal of Hepatology, vol. 60, No. 3, p. 681, 2014, XP028612107, DOI: 10.1016/j.jhep.2013.10.030, Elsevier, Amsterdam, NL.
Athena Kritharis et al., "Hereditary hemorrhagic telangiectasia: diagnosis and management from the hematologist's perspective," Haematologica, vol. 103, No. 9, pp. 1433-1443, May 24, 2018, XP055924426, ISSN: 0390-6078, DOI: 10.3324/haematol.2018.193003.
European Patent Office "Extended European Search Report," issued in European Patent Application No. 19 864 308.2, which is a counterpart to U.S. Appl. No. 17/274,725, issued on Jun. 17, 2022, 13 pages.

* cited by examiner

*Primary Examiner* — Irina Neagu
(74) *Attorney, Agent, or Firm* — Amster, Rothstein & Ebenstein LLP

(57) ABSTRACT

Methods and pharmaceutical compositions comprising one or more mTOR inhibitors such as sirolimus and one or more receptor tyrosine kinase inhibitors such as nintedanib are disclosed for treating vascular lesions and hereditary hemorrhagic telangiectasia.

24 Claims, 6 Drawing Sheets

COMBINED SIROLIMUS AND NINTEDANIB THERAPY FOR VASCULAR LESIONS AND HEREDITARY HEMORRHAGIC TELANGIECTASIA

CROSS-REFERENCE TO RELATED APPLICATIONS

This application is a U.S. national stage entry under 35 U.S.C. § 371 of PCT International Patent Application No. PCT/US2019/052551, filed on Sep. 24, 2019, which claims the benefit of U.S. Provisional Patent Application No. 62/736,564, filed on Sep. 26, 2018, the content of each of which is herein incorporated by reference in its entirety.

STATEMENT OF GOVERNMENT SUPPORT

This invention was made with government support under grant numbers HL 139778 and HL150040 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Arteriovenous malformations (AVMs) are vascular lesions, which form abnormal connections between arteries and veins that omit the capillary system that would normally be interposed between them. Hereditary hemorrhagic telangiectasia (HHT), also known as Osler-Weber-Rendu disease or syndrome, is a hemorrhagic genetic disorder that leads to abnormal blood vessel formations (or vascular lesions), including prominently telangiectases and arteriovenous malformations, in the skin, mucous membranes and organs, such as the liver, lung, gastrointestinal system, and brain of an afflicted subject. In its most severe manifestations, HHT can lead to highly debilitating and life-threatening events, such as severe epistaxis and internal bleeding. HHT is also associated with secondary complications, which include anemia, cerebral abscess and embolism following pulmonary AVMs, as well as high-output cardiac failure consecutive to liver AVMs. The clinical presentation of HHT has been described, for example, in McDonald and Pyeritz (2000).

The present invention addresses the need for treatments of hereditary hemorrhagic telangiectasia, and particularly of attendant vascular lesions, hemorrhage, and anemia.

SUMMARY OF THE INVENTION

The invention provides methods of treating a vascular lesion, such as an arteriovenous malformation, and/or bleeding and/or anemia in subjects in need thereof, including hereditary hemorrhagic telangiectasia (HHT) subjects, comprising administering to the subject sirolimus, or one or more mTOR inhibitors, and nintedanib, or one or more receptor tyrosine kinase (RTK) inhibitors, in therapeutically effective amounts to treat a vascular lesion and/or bleeding and/or anemia in a subject. The invention also provides methods of treating hereditary hemorrhagic telangiectasia in subjects in need thereof comprising administering to the subject sirolimus, or one or more mTOR inhibitors, and nintedanib, or one or more RTK inhibitors, in therapeutically effective amounts to treat abnormal blood vessel formation in a subject.

The invention also provides pharmaceutical compositions comprising sirolimus, or one or more mTOR inhibitors, nintedanib, or one or more RTK inhibitors, and a pharmaceutically acceptable carrier.

DETAILED DESCRIPTION OF THE INVENTION

Figure 1A:
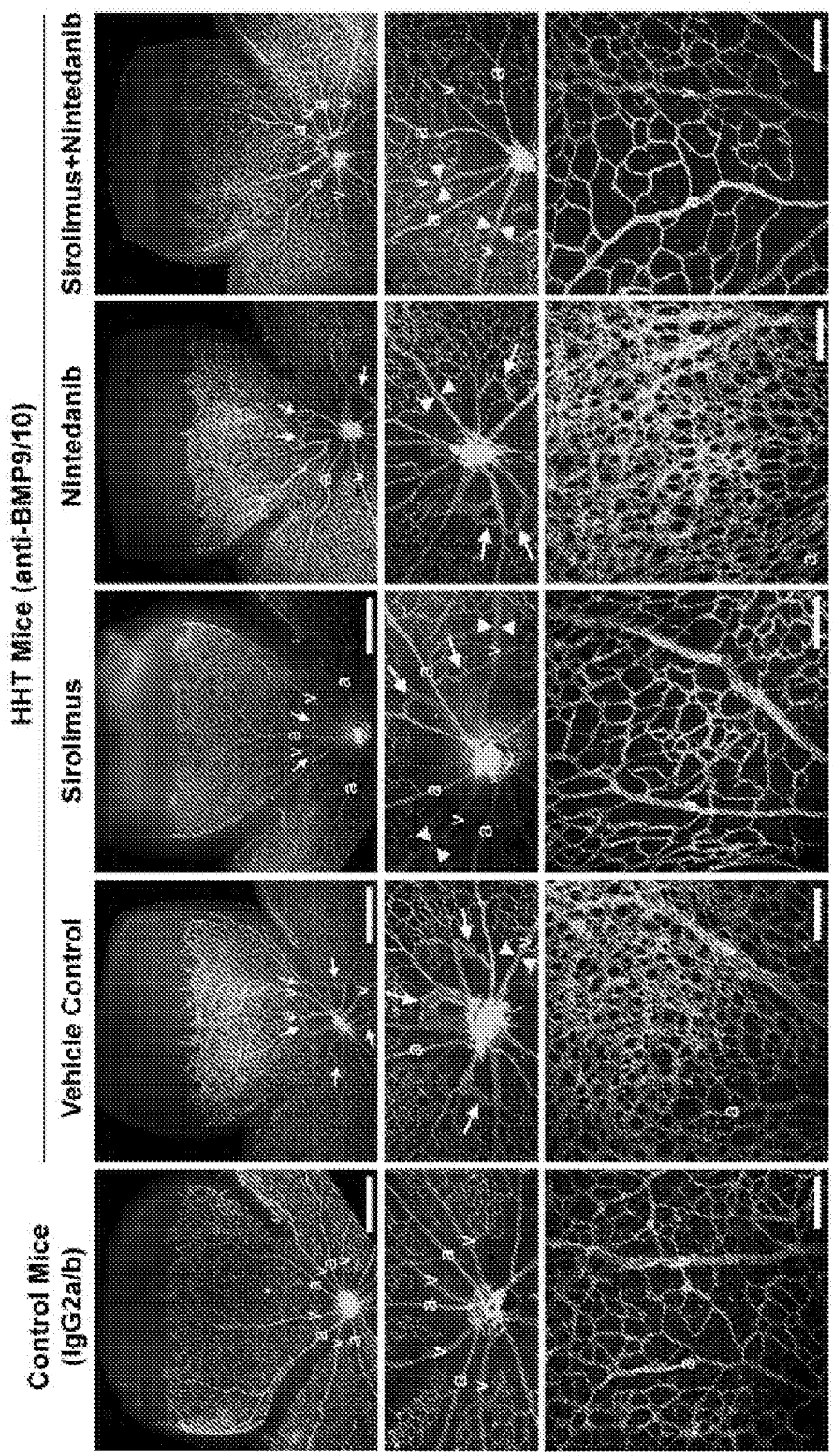
FIG. 1A-1B. Effect of various treatments in a mouse model of hereditary hemorrhagic telangiectasia (HHT). (A) Histological illustrations of harvested retinae from control mice and induced HHT mice given different treatments. a—artery, v—vein. Anti-BMP9/10 refers to induction of HHT in a mouse model. Arrows point to the vascular lesions, i.e., the arteriovenous malformations. Arrowheads illustrate diameters of veins. (B) Effects of different treatments on number and diameter of arteriovenous malformations (AVMs), diameter of veins, and vascular density, including statistical comparisons.

The invention provides a method of treating an arteriovenous malformation, a vascular lesion, bleeding and/or anemia in a subject in need thereof, particularly a subject with Hereditary Hemorrhagic Telangiectasia (HHT), comprising administering to the subject sirolimus and nintedanib in therapeutically effective amounts to treat an arteriovenous malformation, a vascular lesion, bleeding and/or anemia in a subject.

Also provided is a method of treating an arteriovenous malformation, a vascular lesion, bleeding and/or anemia in a subject in need thereof, particularly a subject with HHT, comprising administering to the subject one or more mTOR inhibitors and one or more receptor tyrosine kinase (RTK) inhibitors in therapeutically effective amounts to treat an arteriovenous malformation, a vascular lesion, bleeding and/or anemia in a subject.

The invention also provides a method of treating hereditary hemorrhagic telangiectasia in a subject comprising administering to the subject sirolimus and nintedanib in therapeutically effective amounts to treat abnormal blood vessel formation in a subject.

Also provided is a method of treating hereditary hemorrhagic telangiectasia (HHT) in a subject comprising administering to the HHT subject one or more mTOR inhibitors and one or more receptor tyrosine kinase (RTK) inhibitors in therapeutically effective amounts to treat abnormal blood vessel formation in a HHT subject.

In any of the methods or pharmaceutical compositions disclosed herein, the mTOR inhibitor can be, e.g., one or more of temsirolimus, everolimus, ridaforolimus, tacrolimus and sirolimus. In any of the methods or pharmaceutical compositions disclosed herein, the RTK inhibitor can be, e.g., one or more of pazopanib, sunitinib, sorafenib, erlotinib and nintedanib.

As used herein, to "treat" vascular lesions or abnormal blood vessel formations means to reduce, in a subject, the number, size and/or likelihood of occurrence of the malformation or abnormal formation, as well as to prevent the rupture of these lesions and malformations and the consequent bleeding or hemorrhage and anemia.

Bleeding in subjects, in particular HHT subjects, can occur for example in mucosal lesions, for instance, in the nose or gastrointestinal tract. Bleeding can also occur, for example, in the oral mucosa, retina, liver, lung and/or brain.

The vascular lesion or the abnormal blood vessel formation can be an arteriovenous malformation.

In one embodiment, sirolimus and nintedanib are co-administered to the subject. Sirolimus and nintedanib can be co-administered in the same formulation, or administered in separate formulations. In another embodiment, sirolimus and nintedanib are administered sequentially. Preferably, when administered sequentially, sirolimus and nintedanib are administered within 24 hours of each other.

In one embodiment, one or more mTOR inhibitors and one or more RTK inhibitors are co-administered to the subject. The one or more mTOR inhibitors and the one or more RTK inhibitors can be co-administered in the same formulation, or administered in separate formulations. In another embodiment, the one or more mTOR inhibitors and the one or more RTK inhibitors are administered sequentially. Preferably, when administered sequentially, the one or more mTOR inhibitors and the one or more RTK inhibitors are administered within 24 hours of each other.

In one embodiment, tacrolimus is administered to the subject in a therapeutically effective amount prior to administration of sirolimus and/or nintedanib, or prior to administration of the one or more mTOR inhibitors and/or the one or more RTK inhibitors. In one embodiment, administration of tacrolimus is followed by administration of sirolimus or the one or more mTOR inhibitors, and optionally by administration of nintedanib or the one or more RTK inhibitors. In one embodiment, administration of tacrolimus is followed by administration of nintedanib or the one or more RTK inhibitors, and optionally by administration of sirolimus or the one or more mTOR inhibitors. In one embodiment, tacrolimus is administered to the subject in a therapeutically effective amount in combination with administration of sirolimus and/or nintedanib, or in combination with administration of the one or more mTOR inhibitors and/or the one or more RTK inhibitors. In one embodiment, tacrolimus is administered prior to, or in combination with, sirolimus or the one or more mTOR inhibitors, without administration of nintedanib or the one or more RTK inhibitors. In one embodiment, tacrolimus is administered prior to, or in combination with, nintedanib or the one or more RTK inhibitors, without administration sirolimus or the one or more mTOR inhibitors.

In one embodiment, sirolimus and/or nintedanib, or one or more mTOR inhibitors and/or one or more RTK inhibitors, are the only therapeutic agents administered to the subject for the purpose of treating an arteriovenous malformation, a vascular lesion, bleeding and/or anemia, and/or HHT. In one embodiment, tacrolimus, sirolimus and/or nintedanib, or one or more mTOR inhibitors and/or one or more RTK inhibitors, are the only therapeutic agents administered to the subject for the purpose of treating an arteriovenous malformation, a vascular lesion, bleeding and/or anemia, and/or HHT.

Administration can be systemically or topically. Preferred routes of administration include oral administration, nasal administration, rectal administration and transdermal administration. Any acceptable route of administration can be used. Pharmaceutical compositions designed, for example, for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients. Tablets, pills, capsules, troches and the like may also contain binders, recipients, disintegrating agent, lubricants, sweetening agents, and flavoring agents.

Pharmaceutical compositions useful for the present invention can also be administered parenterally such as, for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

Nasal administration includes administering the composition to the mucous membranes of the nasal passage or nasal cavity of the patient. Pharmaceutical compositions for nasal administration include compositions prepared by well-known methods to be administered, for example, as a nasal spray, nasal drop, suspension, gel, ointment, cream or powder. Administration of the composition may also take place using a nasal tampon or nasal sponge.

The subject can be any mammal and is preferably a human subject.

The invention also provides a pharmaceutical composition comprising therapeutically effective amounts of sirolimus and nintedanib, and a pharmaceutically acceptable carrier. The invention also provides a pharmaceutical composition comprising therapeutically effective amounts of one or more mTOR inhibitors and one or more RTK inhibitors, and a pharmaceutically acceptable carrier. The pharmaceutical composition can comprise a therapeutically effective amount of tacrolimus. Preferably, the pharmaceutical composition is formulated in amounts effective to treat an arteriovenous malformation, a vascular lesion, bleeding and/ or anemia in a subject. Bleeding can occur, for example, in the nose, oral mucosa, lung, liver, gastrointestinal tract, brain and/or retina.

In any of the methods or compositions disclosed herein, sirolimus and/or tacrolimus can be administered in a dose of 0.03-1 mg/kg body weight/day for a human subject, and preferably in a dose of 0.04 mg/kg body weight/day.

In any of the methods or compositions disclosed herein, nintedanib can be administered in a dose of 0.02-5 mg/kg body weight/day for a human subject, and preferably in a dose of 0.5 mg/kg body weight/day.

As used herein, a "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, additive solution-3 (AS-3), saline, Ringer's solution, lactated Ringer's solution, Locke-Ringer's solution, Krebs Ringer's solution, Hartmann's balanced saline solution, emulsions such as oil/water emulsion, various types of wetting agents and/or heparinized sodium citrate acid dextrose solution. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000). The pharmaceutically acceptable carrier used can depend on the route of administration.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Overview

Figure 1B:
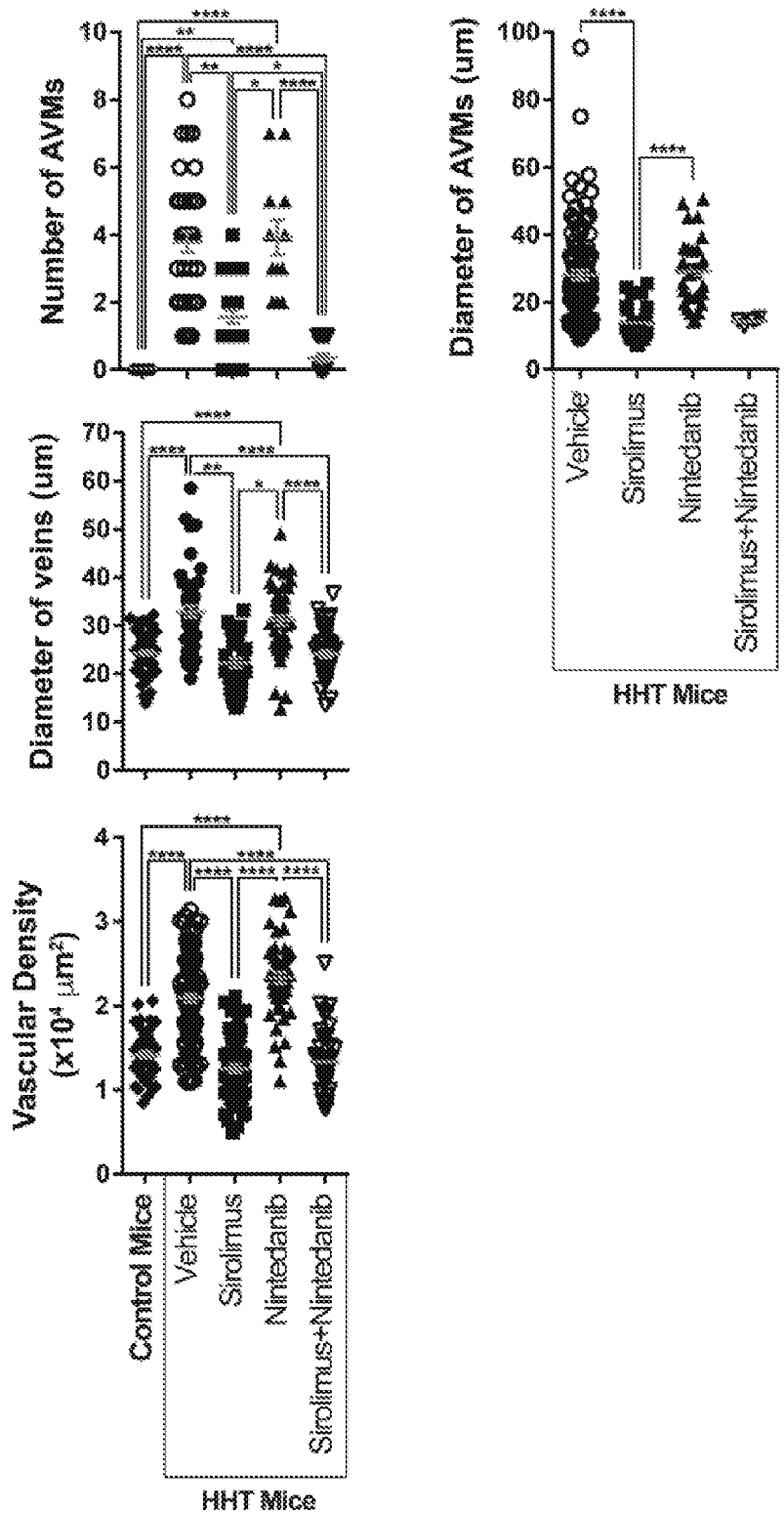
Figure 2A:
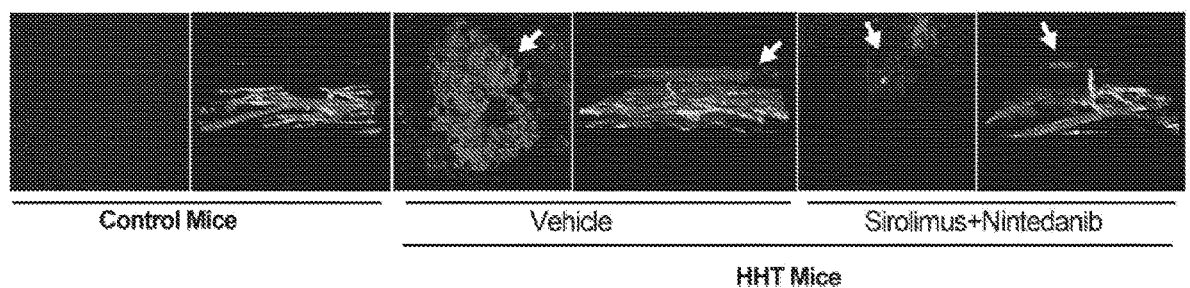
FIG. 2A-2B. Effect of treatment with sirolimus and nintedanib in a mouse model of hereditary hemorrhagic telangiectasia (HHT). (A) Histological illustrations of retinal bleeding. (B) Effect of treatment with sirolimus and nintedanib on retinal bleeding.
Figure 2B:
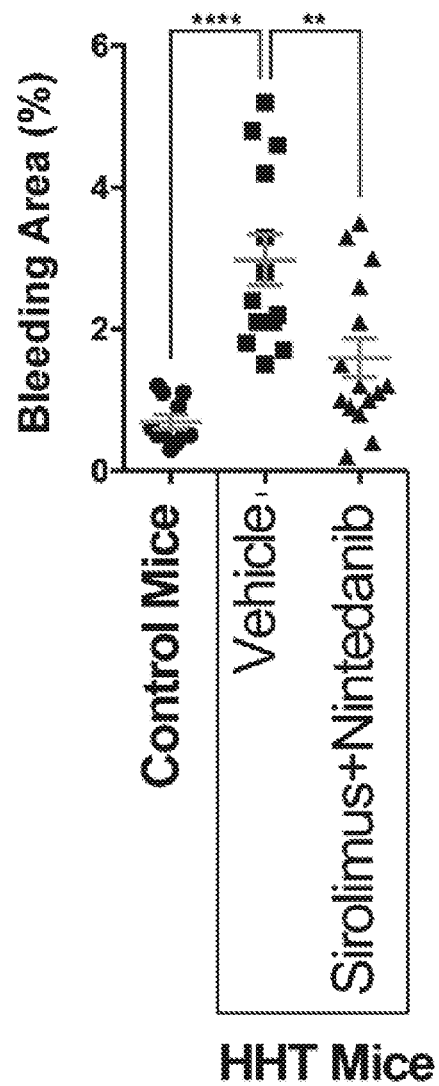
Figure 3A:
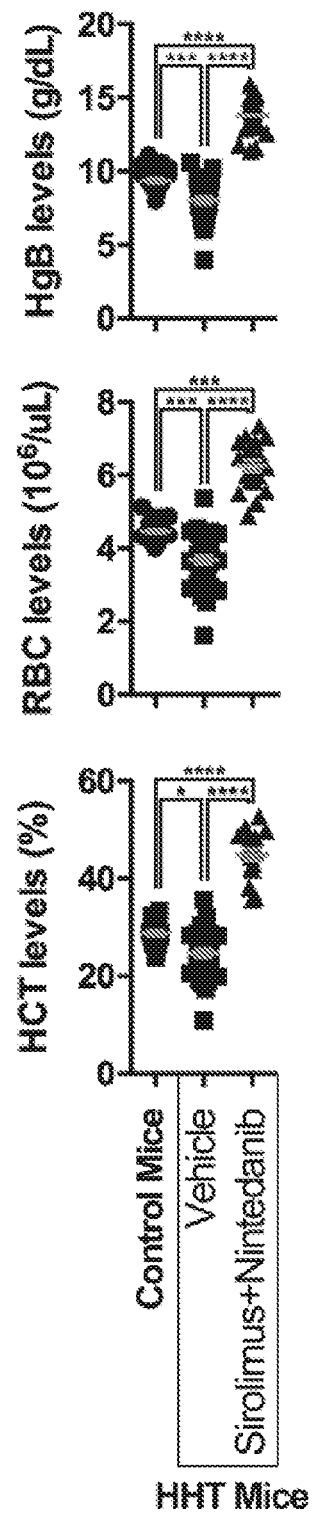
FIG. 3A-3B. Effect of treatment with sirolimus and nintedanib in a mouse model of hereditary hemorrhagic telangiectasia (HHT). (A) Effect of treatment with sirolimus and nintedanib on hemoglobin, red blood cell, and hematocrit levels. (B) Effect of treatment with sirolimus and nintedanib on spleen/body weight and heart/body weight ratios.
Figure 3B:
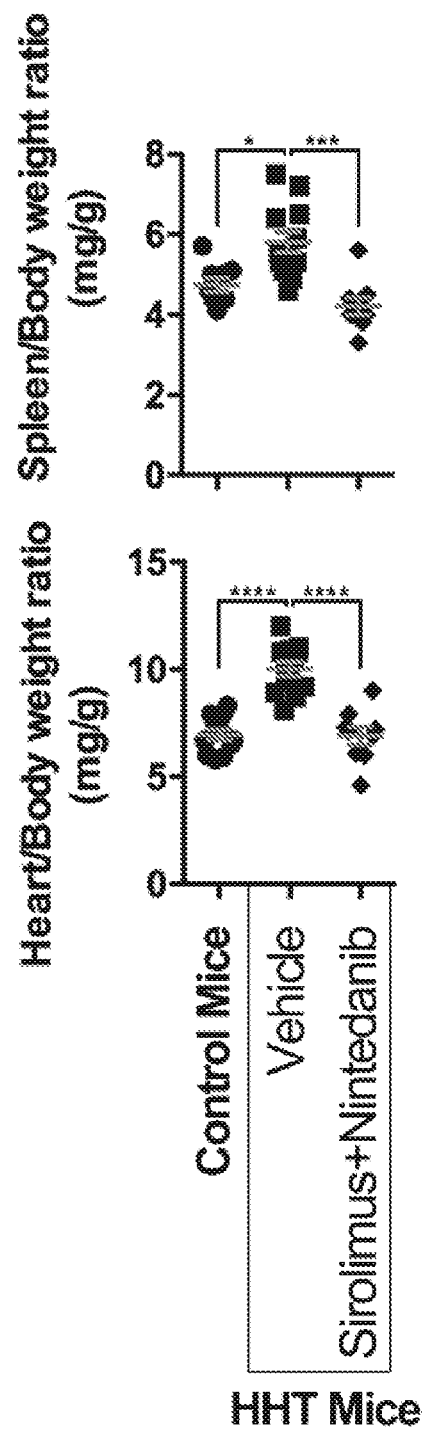

The effects of treatment with the mTOR (mechanistic target of rapamycin, also known as mammalian target of rapamycin) inhibitor, sirolimus, and the receptor tyrosine kinase inhibitor, nintedanib, in a mouse model of hereditary hemorrhagic telangiectasia (HHT) are illustrated in FIGS. 1-3.

The HHT mouse model, which uses the transmammary route for administering BMP9 and BMP10 blocking antibodies to nursing mouse pups, referred to as the transmammary-treated BMP9/10 immunoblocked (tBMP9/10ib) mice, has been previously described (Ruiz et al., 2016, 2017).

While treatment with either sirolimus or nintedanib, administered alone, only moderately improve the pathology in HHT mice, combination treatment showed that sirolimus and nintedanib robustly synergized to prevent, and also reverse, abnormal vascularization (FIGS. 1A and 1B) and AVMs (FIGS. 1A and 1B) and to avert bleeding (FIGS. 2A and 2B) in HHT mice.

Drug combination efficiently reduced vascular pathology in the liver, the lung and the mucosal tissue, and prevented tissue ischemia. Drug combination efficiently prevented bleeding (FIGS. 2A and 2B) and anemia (FIG. 3A), as well as normalized splenomegaly (spleen/body weight ratio, FIG. 3B) and cardiomegaly (heart/body weight ratio, FIG. 3B), two important sequelae of anemia.

Sirolimus/nintedanib combination blocks vascular pathology in HHT mice. Mice were injected or not (vehicle control) with sirolimus (0.5 mg/kg/day), nintedanib (0.3 mg/kg/day), or a combination thereof (sirolimus+nintedanib), and treated or not (control mice) with BMP9/BMP10 blocking antibodies to induce HHT pathology. The sirolimus/nintedanib combination treatment significantly corrected vascular pathology, while the two drugs administered alone only had a moderate-to-negligible effect.

Sirolimus/nintedanib combination prevents and treats bleeding in HHT mice. The sirolimus/nintedanib combination treatment significantly reduced bleeding intensity.

Sirolimus/nintedanib combination also prevents and treats anemia in HHT mice. Sirolimus/nintedanib combination treatment fully normalized anemia and prevented both splenomegaly and cardiomegaly.

Sirolimus/nintedanib combination therapy was also shown to reduce gastrointestinal (GI) bleeding and anemia using a second HHT mouse model, the adult Alk1 inducible knockout mouse. This model has been previously described (Kim et al. 2017; Park et al. 2008).

Mechanistically, vascular pathology in the affected HHT mouse tissues was accompanied by a robust activation in endothelial cells (ECs) of mTOR and VEGFR2 (vascular endothelial growth factor receptor 2). Sirolimus acted by inhibiting mTOR activation, while nintedanib inhibited VEGFR2 activation.

In primary human ECs in vitro, including in HHT patient-derived blood outgrowth ECs, sirolimus potently inhibited mTOR.

These data show that concurrent treatment with sirolimus in combination with nintedanib produces a synergistic correction of endothelial mTOR and VEGFR2 pathways and efficiently opposes HHT pathogenesis by preventing and reversing vascular pathology and associated bleeding and anemia, as exemplified in two HHT mouse models. Sirolimus in combination with nintedanib is thus a new treatment to provide therapeutic benefit in HHT patients.

Sirolimus (Siro) and Nintedanib (Nin) Combination Prevents Vein Dilation, Hypervascularization, and AVM Development in the Retina of the tBMP9/10ib Mice.

Studies were conducted prior to these experiments to determine the appropriate dosing and injection schedule of the drugs in pups. The highest dose of Siro that did not affect normal vascular development was chosen [0.5 mg/kg, intraperitoneal (i.p.) injection of the pups, assessed in the neonatal retina]. Similarly, in order to prevent changes in retinal vascular development, it was determined that Nin should be given every third day and not before P5. With this schedule for Nin injection, the highest dose of the drug that did not affect physiological vascular development was determined to be 0.3 mg/kg. Co-administration of Siro and Nin (Siro+Nin) at these dosing and injection schedules did not also significantly affect normal vascular growth, indicating that physiological angiogenesis in the retina was not inhibited by the drug combination. At this dosing, LC-MS analyses measured average serum concentrations of 9.0 nM Siro and 5.3 nM Nin in the injected P6 pups.

As described before (Ruiz et al., 2016, 2017), vascular pathology in pups was initiated at postnatal day 3 (P3) by one i.p. injection of the dams with anti-BMP9/10 antibodies. Mouse pups were administered preventively and daily with Siro from P3 to P5 (0.5 mg/kg, i.p.) and with Nin at P5 (0.3 mg/kg, i.p.). Mice were then analyzed at P6, a time point at which retinal vessel dilation, hypervascularization, and AVMs can readily be observed and quantified in this model. In the tBMP9/10ib retinas, Siro significantly reduced AVM number and AVM diameter. In addition, as observed previously for Tac at the same dosing (0.5 mg/kg, P3-P5, i.p.) (Ruiz et al., 2017), Siro prevented vein dilation and the increase in density of the vascular plexus. In contrast, Nin at the tested dosing failed to reduce any of the investigated vascular defects of the tBMP9/10ib retinas.

Although Siro treatment was able to significantly reduce AVM number and size, its preventive effect was only partial (AVM number, mean=3.79±0.30 in DMSO-treated tBMP9/10ib retinas vs. mean=1.57±0.19 in Siro-treated tBMP9/10ib retinas, P≤0.01). It was tested whether the VEGFR2 inhibitor Nin could increase Siro potency in preventing AVMs. Combination treatment with the two drugs resulted in a significant increase of Siro anti-AVM effect (AVM number after treatment, mean=0.35±0.11, P≤0.0001 vs. DMSO-treated tBMP9/10ib retinas, and P≤0.05 vs. Siro-treated tBMP9/10ib retinas). Siro+Nin combination did not further increase the effect of Siro on vein dilation and vascular density, as Siro alone was sufficient to fully correct these two defects. Measurement of the diameter of the few remaining AVMs identified in the retina of the Siro+Nin-treated mice also revealed no difference compared to treatment with Siro alone. Together these data in tBMP9/10ib mice show that Siro fully normalized vein dilation and hypervascularization, and significantly lowered AVM number and size in the retina. Furthermore and more strikingly, Nin significantly strengthened the anti-AVM effect of Siro.

Siro+Nin Prevents Anemia and Retinal Bleeding in tBMP9/10ib Mice.

Pathology progression was assessed in tBMP9/10ib pups at P9. As before, vascular pathology in pups was initiated at P3 by one i.p. injection of the dams with anti-BMP9/10 antibodies. Complete blood count (CBC) revealed significant reductions in hematocrit level, red blood cell (RBC) number, and hemoglobin level, indicative of anemia in P9 tBMP9/10ib pups. Furthermore, severe cardiomegaly and splenomegaly developed in tBMP9/10ib mice. Splenomegaly was accompanied by an expansion of the red pulp, indicating the presence of splenic erythropoietic stress response consecutive to anemia. These data prompted an investigation as to whether tBMP9/10ib mice were actively bleeding. Inspection of the retinas using whole-mount immunohistochemistry (IHC) with an antibody directed against the RBC marker, Ter119, revealed the presence of strongly immunoreactive patches in multiple areas of the tBMP9/10ib retinas. Single-cell resolution confocal analyses and 3D reconstruction showed the presence of RBC patches outside the tBMP9/10ib retinal vasculature. Interestingly, isolectin B4-positive projections could clearly be identified near the center of some of these RBC accumulations, suggesting that they might represent transversal vascular projections at the origin of the bleeding. Treatment of the tBMP9/10ib mice with Siro+Nin from P3 to P8 significantly reduced the area occupied by retinal bleeding and fully prevented the decrease in hematocrit level, RBC number, and hemoglobin level, as well as blocked cardiomegaly, splenomegaly, and the loss of splenic architecture. Thus, Siro+Nin combination treatment prevented anemia and retinal bleeding in tBMP9/10ib mice.

Although a modest decrease in heart rate was measured by doppler ultrasonography upon drug treatment in tBMP9/10ib mice, heart rate was overall not significantly changed in DMSO-treated and Siro+Nin-treated tBMP9/10ib pups, compared to normal pups. In addition, no significant defects in cardiac output or pulmonary arterial pressure measures were found between all groups. These data demonstrate that basic cardiac function is normal in tBMP9/10ib pups, at least until P9, and that Siro+Nin combination is therefore unlikely to act on the vasculature by changing cardiac output.

Siro+Nin Reverses Vascular Pathology in tBMP9/10ib Mice.

The retinal vasculature of P9 tBMP9/10ib mice treated or not with Siro+Nin were then analyzed. On average ~4 AVMs were detected in tBMP9/10ib mice, indicating that no additional AVMs developed between P6 (mean=3.79±0.30) and P9. Strikingly, while Siro+Nin-treated P6 mice still contained some AVMs (n=0.35±0.11), the P9 tBMP9/10ib mouse retinas that were treated with the drugs for 3 additional days were devoid of AVMs. In addition, the 6-day-Siro+Nin treatment (P3-P8), as was observed after the 3-day-Siro+Nin treatment (P3-P5), fully prevented vein dilation and hypervascularization. LC-MS analyses measured an increase in average drug concentrations in the pup serum between P6 and P9: from 9.0 nM to 22.6 nM Siro and from 5.3 nM to 24.7 nM Nin, indicating that three additional days of drug treatment led to an accumulation of the drugs in the circulation.

These data suggest that Siro+Nin treatment might also reverse existing AVMs, since some AVMs disappeared between P6 and P9. To directly address this possibility, a protocol was implemented that started the drug treatment once retinal vascular pathology was established. Specifically, pathology was induced as before at P3 and pups were then treated at P6 with Siro+Nin, a time point where there is robust vein dilation, hypervascularization, and ~4 AVMs per retina. Pups were treated for 3 days, from P6 to P8 (P6-P8), and analyzed at P9. Siro+Nin administered after pathology induction significantly reduced overall vascular pathology, including AVM number, AVM size, vein dilation, and vascular density. In addition, P6-P8 Siro+Nin treatment significantly increased hematocrit level, RBC number, and hemoglobin level in anemic tBMP9/10ib mice.

Since disease induction is triggered by only one i.p. injection at P3 of anti-BMP9/10 antibodies, it was verified that the observed effects of Siro+Nin in P9 pups were not facilitated by a disappearance of the disease-causing anti-BMP9/10 blocking antibodies from the pup circulation. Using specific anti-BMP9 and anti-BMP10 antibody ELISAs, serum antibody concentrations were stable between P6 and P9, and reached ~70 µg/mL for the anti-BMP9 antibody and ~85 µg/mL for the anti-BMP10 antibody. Thus, the disease-causing effects of the anti-BMP9/10 antibodies was maintained between P6 and P9, and therefore, the drug combination effect on pre-existing AVMs occurred in a maintained pathogenic environment. Taken together, these findings demonstrate that Siro+Nin combination treatment not only prevented, but also reversed, the retinal vascular pathology of the tBMP9/10ib mice.

Siro+Nin Prevents Vascular Pathology in the Oral Mucosa and Lungs of the tBMP9/10ib Mice.

The oral mucosa and lungs are major sites of vascular lesion development in HHT patients. It was investigated whether vascular defects are observed in these tissues of the P9 tBMP9/10ib mice. Injections of latex blue dye in the blood circulation were used to visualize vascular pathology. In the tBMP9/10ib mouse tongue and palate, mucosal vein dilation and hyperproliferative vascular defects were clearly identified after latex dye injection. Significant enlargements of the lingual and greater palatine vessels could be measured, compared to control tongues and palates. In the lungs, the dye invaded a hypervascularized network of dilated small vessels throughout the lobar system and revealed an enlargement of the main pulmonary vessels of the tBMP9/10ib mice. Siro+Nin treatment of the tBMP9/10ib mice significantly and efficiently prevented the hyperproliferative vascular pathology and vessel dilation phenotype observed in the tongue, palate mucosa, and lungs. Thus, Siro+Nin combination reduced vascular pathology in the oral mucosa and lungs.

Siro+Nin Corrects a Gene Expression Signature and Prevents Vascular Pathology in the Liver of the tBMP9/10ib Mice.

The liver is the most vascularized organ of the body and is a major site of vascular lesion development in HHT patients, more specifically in HHT2 patients (Letteboer, 2006). It was next investigated whether vascular defects could be observed in the liver of the P9 tBMP9/10ib mice. Vascular pathology induction and drug treatments in pups were performed as above. Latex dye tissue invasion was enhanced in the tBMP9/10ib liver and revealed a significant enlargement of the hepatic vessels. Hematoxylin and eosin (H&E) staining showed the presence of marked local liver injury, characterized by the presence of significant hepatocyte vacuolation and hepatocellular necrosis, a pathology that could result from ischemic events.

To gain insight into the mechanism of liver injury, a proteome array for angiogenesis-related factors was performed. This screen identified plasminogen activator inhibitor 1 (PAI-1) as a protein strongly upregulated in the tBMP9/10ib liver, compared to livers from control mice. PAI-1 is of interest because it is upregulated during hypoxia (Kietzmann et al., 1999), and might thus represent a response to ischemia. PAI-1 elevation in the tBMP9/10ib liver was confirmed by Western blot (WB) and IHC analyses. To verify that hypoxia is occurring in the tBMP9/10ib liver, tissue sections were stained for hypoxia-inducible factor-1a (HIF-1α), a transcriptional factor marker and master regulator of hypoxia (Semenza et al., 2000). A strong upregulation of liver HIF-1α expression was found in tBMP9/10ib mice, compared to control mice. These data show that tBMP9/10ib mice develop a robust vascular pathology in the liver. Strikingly, Siro+Nin treatment of the tBMP9/10ib mice significantly prevented the hyperproliferative vascular pathology and vessel dilation phenotype of the liver. In addition, Siro+Nin efficiently reduced hepatocyte vacuolation and necrosis, as well as prevented the overexpression of PAI-1 and HIF-1α in the liver of the tBMP9/10ib mice. Together, these results demonstrate that Siro+Nin combination prevented vascular pathology in the liver, as well as blocked liver disease in tBMP9/10ib mice.

To further test the therapeutic potential of the Siro+Nin combination, it was determined: (1) whether gene expression changes could be detected in the tBMP9/10ib whole-liver tissue and (2) whether treatments with the two drugs (administered alone or in combination) could correct these transcriptomic changes. When the transcript expression changes (measured as log fold change values, log FC) were plotted in tBMP9/10ib pups vs. normal controls, against the transcript expression log FCs obtained after treating the tBMP9/10ib pups with Siro+Nin vs. vehicle (DMSO), an inverse correlation was found for Siro+Nin treatment ($r2=0.380$, $P<0.001$). An inverse correlation indicates that Siro+Nin treatment normalized some of the changes observed in the disease model (tBMP9/10ib pups) compared to normal controls. When the same comparison was done for Siro and Nin administered alone, a weaker correlation was measured ($r2=0.193$ and $0.190$, respectively, $P<0.001$). These results indicate that Siro+Nin combination better corrected the expression changes of liver transcripts detected in the tBMP9/10ib mice, than either drug administered alone.

To illustrate the synergistic effect of the Siro and Nin treatments on transcript expression, transcripts were identified that were differentially changed by the drug treatments in the tBMP9/10ib liver (n=6-9 biological replicates/group, false discovery rate (FDR) ≤0.5%, log average expression >-5). A synergistic effect exists between Siro and Nin treatments at the gene expression level, and that this effect could normalize a subset of deregulated transcripts in the tBMP9/10ib liver. A function enrichment analysis of the identified subset of normalized transcripts revealed a significant network of genes involved in cell and protein metabolism (e.g., Uba6, Tmem56, mt-Nd3, Kdmlb, Gcic, Prkd3; GeneMANIA (Warde-Farley et al., 2010)), a response indicative of strong gene expression changes consecutive to liver injury and changes in cell homeostasis and cell stress.

Together, these transcriptomic data show that Siro and Nin treatments synergized and partially opposed a deregulated gene expression signature detected in the tBMP9/10ib liver. These results are important because they confirm the interaction and combination efficacy of the two drugs in reducing overall vascular pathology in tBMP9/10ib mice.

Siro+Nin Reduces GI Bleeding and Anemia in Adult Alk1 iKO Mice.

The effect of the drug combination was evaluated in an adult Alk1 inducible knockout (iKO) mouse model (R26CreER/+; Alk12f/2f). In this model, ALK1 deficiency is induced by tamoxifen administration to generate severe gastrointestinal (GI) bleeding and anemia in 9 days (Kim et al. 2017; Park et al. 2008). Daily treatment with the same doses of Siro+Nin used for the tBMP9/10ib mice (0.5 mg/kg Siro and 0.3 mg/kg Nin, i.p.), starting at the time of tamoxifen injection, significantly reduced GI bleeding and significantly increased hematocrit level, RBC number, and hemoglobin level, compared to the vehicle-treated Alk1 iKO controls.

In tBMP9/10ib Mice, Siro and Nin Prevent Endothelial Overactivation of mTOR and VEGFR2, Respectively.

mTOR signaling was assessed in tBMP9/10ib mice by measuring the levels of phospho-mTOR (p-mTOR) and phospho-S6 (p-S6) in the liver and retina. WB analyses revealed robust increases in p-mTOR and p-S6 levels in whole-liver homogenates isolated from tBMP9/10ib mice, compared to control mice. Treatment with Siro (alone or in combination with Nin) blocked S6 phosphorylation and normalized p-mTOR levels in the tBMP9/10ib mouse liver. Further examination of the tBMP9/10ib retinal tissue confirmed the presence of strong p-S6 immunoreactivity in the AVMs, which could significantly be blocked by Siro treatment of the mice.

A significant elevation of activated phospho-VEGFR2 (p-VEGFR2) was detected in protein homogenates of liver ECs isolated from tBMP9/10ib mice and in the tBMP9/10ib mouse retina, which was significantly inhibited by Nin treatment of the mice. Drug combination did not interfere with the inhibitory effect of Nin on p-VEGFR2. As observed upon treatment with Nin alone, Siro+Nin fully inhibited VEGF-induced VEGFR2 activation in primary ECs. Altogether, these data confirmed that endothelial mTOR and VEGFR2 are overactivated in tBMP9/10ib mice and that Siro and Nin can respectively and efficiently block these signaling deregulations in vivo.

REFERENCES

Kietzmann T, Roth U, Jungermann K. Induction of the plasminogen activator inhibitor-1 gene expression by mild hypoxia via a hypoxia response element binding the hypoxia-inducible factor-1 in rat hepatocytes. Blood 1999; 94(12):4177-4185.
Kim Y H et al. Selective effects of oral antiangiogenic tyrosine kinase inhibitors on an animal model of hereditary hemorrhagic telangiectasia. J. Thromb. Haemost. 2017; 15(6):1095-1102.
Letteboer T G W et al. Genotype-phenotype relationship in hereditary haemorrhagic telangiectasia. J. Med. Genet. 2006; 43(4):371-377.
McDonald J, Pyeritz R E. Hereditary Hemorrhagic Telangiectasia. In: Adam M P, Ardinger H H, Pagon R A, Wallace S E, Bean L J H, Stephens K, Amemiya A, editors. GeneReviews®. Seattle (Wash.): University of Washington, Seattle; 1993-2018. 2000 Jun. 26. PMID: 20301525.
Park S O et al. ALK5- and TGFBR2-independent role of ALK1 in the pathogenesis of hereditary hemorrhagic telangiectasia type 2. Blood 2008; 111(2):633-642.
Ruiz S et al. A mouse model of hereditary hemorrhagic telangiectasia generated by transmammary-delivered immunoblocking of BMP9 and BMP10. Sci. Rep. 2016; 5:37366.
Ruiz S et al. Tacrolimus rescues the signaling and gene expression signature of endothelial ALK1 loss-of-function and improves HHT vascular pathology. Hum. Mol. Genet. 2017; 26(24):4786-4798.
Semenza G L. HIF-1: mediator of physiological and pathophysiological responses to hypoxia. J. Appl. Physiol. 2000; 88(4):1474-1480.
Warde-Farley D et al. The GeneMANIA prediction server: biological network integration for gene prioritization and predicting gene function. Nucleic Acids Res. 2010; 38(Web Server issue):W214-20.

What is claimed is:

1. A method of treating one or more of an arteriovenous malformation, a vascular lesion and bleeding in a subject who has hereditary hemorrhagic telangiectasia (HHT) comprising administering to the subject sirolimus and nintedanib in therapeutically effective amounts to treat an arteriovenous malformation, a vascular lesion and/or bleeding in the subject, wherein sirolimus and nintedanib are the only therapeutic agents administered to the subject.

2. A method of treating hereditary hemorrhagic telangiectasia (HHT) in a subject in need thereof comprising administering to the HHT subject sirolimus and nintedanib in therapeutically effective amounts to treat abnormal blood vessel formation in the subject, wherein sirolimus and nintedanib are the only therapeutic agents administered to the subject.

3. The method of claim 1, wherein sirolimus and nintedanib are co-administered to the subject.

4. The method of claim 3, wherein sirolimus and nintedanib are co-administered in the same formulation.

5. The method of claim 1, wherein sirolimus and nintedanib are administered sequentially.

6. The method of claim 5, wherein sirolimus and nintedanib are administered within 24 hours of each other.

7. The method of claim 1, wherein tacrolimus is administered to the subject in a therapeutically effective amount prior to administration of sirolimus and nintedanib.

8. The method of claim 1, wherein administration is by oral administration, by nasal administration, by rectal administration or transdermally.

9. The method of claim 1, wherein the subject is a human.

10. The method of claim 1, wherein sirolimus is administered in a dose of 0.03-1 mg/kg body weight/day.

11. The method of claim 10, wherein sirolimus is administered in a dose of 0.04 mg/kg body weight/day.

12. The method of claim 1, wherein nintedanib is administered in a dose of 0.02-5 mg/kg body weight/day.

13. The method of claim 12, wherein nintedanib is administered in a dose of 0.5 mg/kg body weight/day.

14. The method of claim 7, wherein tacrolimus is administered in a dose of 0.03-1 mg/kg body weight/day.

15. The method of claim 1, wherein bleeding occurs in the nose, oral mucosa, lung, liver, gastrointestinal tract, brain and/or retina.

16. The method of claim 2, wherein sirolimus and nintedanib are co-administered to the subject.

17. The method of claim 16, wherein sirolimus and nintedanib are co-administered in the same formulation.

18. The method of claim 2, wherein sirolimus and nintedanib are administered sequentially.

19. The method of claim 18, wherein sirolimus and nintedanib are administered within 24 hours of each other.

20. The method of claim 2, wherein tacrolimus is administered to the subject in a therapeutically effective amount prior to administration of sirolimus and nintedanib.

21. The method of claim 2, wherein the subject is a human.

22. The method of claim 2, wherein sirolimus is administered in a dose of 0.03-1 mg/kg body weight/day.

23. The method of claim 2, wherein nintedanib is administered in a dose of 0.02-5 mg/kg body weight/day.

24. The method of claim 20, wherein tacrolimus is administered in a dose of 0.03-1 mg/kg body weight/day.

* * * * *

UNITED STATES PATENT AND TRADEMARK OFFICE
CERTIFICATE OF CORRECTION

| | |
|---|---|
| PATENT NO. | : 12,239,636 B2 |
| APPLICATION NO. | : 17/274725 |
| DATED | : March 4, 2025 |
| INVENTOR(S) | : Philippe Marambaud |

Page 1 of 1

It is certified that error appears in the above-identified patent and that said Letters Patent is hereby corrected as shown below:

In the Specification

In Column 1, Lines 17-22:
"This invention was made with government support under grant numbers HL 139778 and HL150040 awarded by the National Institutes of Health. The government has certain rights in the invention."

Should read:
-- This invention was made with government support under grant numbers HL 139778 and HL150040 awarded by the National Institutes of Health and grant number W81XWH-17-1-0429 awarded by the Department of Defense. The government has certain rights in the invention. --.

Signed and Sealed this
Tenth Day of June, 2025

Coke Morgan Stewart
*Acting Director of the United States Patent and Trademark Office*